United States Patent
Cho

(10) Patent No.: US 9,820,831 B2
(45) Date of Patent: Nov. 21, 2017

(54) DENTAL IMPLANT FIXTURE CAPABLE OF EASILY RECEIVING BLOOD

(71) Applicant: Sang Choon Cho, New York, NY (US)

(72) Inventor: Sang Choon Cho, New York, NY (US)

(73) Assignee: EBI Inc. (KR)

( * ) Notice: Subject to any disclaimer, the term of this patent is extended or adjusted under 35 U.S.C. 154(b) by 0 days.

(21) Appl. No.: 15/144,408

(22) Filed: May 2, 2016

(65) Prior Publication Data

US 2016/0242875 A1 Aug. 25, 2016

Related U.S. Application Data

(63) Continuation of application No. PCT/KR2014/010466, filed on Nov. 4, 2014.

(30) Foreign Application Priority Data

Mar. 5, 2014 (KR) ........................ 10-2014-0026216

(51) Int. Cl.
*A61C 8/00* (2006.01)
*A61C 8/02* (2006.01)

(52) U.S. Cl.
CPC .......... *A61C 8/0006* (2013.01); *A61C 8/0009* (2013.01); *A61C 8/0024* (2013.01); *A61C 8/0031* (2013.01)

(58) Field of Classification Search
CPC ....... A61C 8/005; A61C 8/006; A61C 8/0022; A61C 8/0069; A61C 8/0089; A61C /
USPC .................................................. 433/172–176
See application file for complete search history.

(56) References Cited

U.S. PATENT DOCUMENTS

| 4,531,915 | A | * | 7/1985 | Tatum, Jr. ............ | A61C 8/0018 433/173 |
| 4,895,515 | A | * | 1/1990 | Axelsson ............... | A61C 17/00 433/166 |
| D342,314 | S | * | 12/1993 | Miller ......................... | D24/156 |
| 5,759,034 | A | | 6/1998 | Daftary | |
| 5,785,525 | A | * | 7/1998 | Weissman ............ | A61C 8/0018 433/174 |
| 5,842,865 | A | * | 12/1998 | Bassett ................ | A61C 8/0024 433/174 |

(Continued)

FOREIGN PATENT DOCUMENTS

| KR | 200433571 Y1 | 12/2006 |
| KR | 100983919 B1 | 9/2010 |
| KR | 101234567 B1 | 2/2013 |

*Primary Examiner* — Cris L Rodriguez
*Assistant Examiner* — Matthew Saunders
(74) *Attorney, Agent, or Firm* — St Onge Steward Johnston and Reens LLC

(57) ABSTRACT

A dental implant fixture as a fixture implanted in an alveolar bone to be an artificial tooth root includes a main body vertically extending long along a center axis, at least part of the main body being implanted in the alveolar bone, and a cutting face formed on an outer circumferential surface of the main body to secure a space for accommodating blood when the main body is implanted in the alveolar bone. The dental implant fixture does not apply excessive pressure to a cortical bone of an alveolar bone when being inserted into an implantation hole, and is capable of rapidly regenerating the alveolar bone by accommodating a large amount of blood inside the implantation hole.

5 Claims, 6 Drawing Sheets

(56) References Cited

U.S. PATENT DOCUMENTS

| | | | | |
|---|---|---|---|---|
| 6,042,376 | A * | 3/2000 | Cohen | A61C 5/023 |
| | | | | 433/102 |
| 6,048,204 | A * | 4/2000 | Klardie | A61C 8/0022 |
| | | | | 433/174 |
| 6,402,517 | B1 * | 6/2002 | Hozumi | A61C 8/0012 |
| | | | | 433/173 |
| 8,899,980 | B2 * | 12/2014 | Chen | A61C 1/087 |
| | | | | 433/165 |
| 2003/0165796 | A1 * | 9/2003 | Carmichael | A61C 8/0024 |
| | | | | 433/174 |
| 2003/0232308 | A1 * | 12/2003 | Simmons, Jr. | A61C 8/0031 |
| | | | | 433/173 |
| 2008/0020349 | A1 * | 1/2008 | Dricot | A61C 8/0012 |
| | | | | 433/174 |
| 2008/0131840 | A1 * | 6/2008 | Chen | A61C 8/0022 |
| | | | | 433/174 |
| 2009/0130631 | A1 * | 5/2009 | Chen | A61C 8/0022 |
| | | | | 433/174 |
| 2010/0330534 | A1 | 12/2010 | Hyun | |
| 2013/0316303 | A1 * | 11/2013 | Weissman | A61C 8/0018 |
| | | | | 433/174 |
| 2014/0242546 | A1 * | 8/2014 | Babiner | A61C 8/0069 |
| | | | | 433/174 |

\* cited by examiner

DENTAL IMPLANT FIXTURE CAPABLE OF EASILY RECEIVING BLOOD

FIELD OF THE INVENTION

The present invention relates to a dental implant fixture, and more particularly, to a dental implant fixture, which does not apply excessive pressure to a cortical bone of an alveolar bone when being inserted into an implantation hole, and is capable of rapidly regenerating the alveolar bone by accommodating a large amount of blood inside the implantation hole.

BACKGROUND OF THE INVENTION

Dental implants, which are referred to as artificial teeth or third teeth, are a dental treatment method for restoring a function of a natural tooth by implanting a bio-adaptive implant main body into a portion having tooth deficiency or a jawbone where a tooth is removed.

An implant generally includes a fixture that becomes an artificial tooth root by being implanted in an alveolar bone, an abutment for an implant that is an abutment post by being screw-coupled to an upper end portion of the fixture, and a crown that is a prosthesis having a tooth shape and is coupled to an upper end portion of the abutment.

An example of a dental implant fixture 1 according to a related art is illustrated in FIG. 7. The dental implant fixture 1 may include a main body 2 that is a cylindrical screw portion vertically extending long and at least a part of the main body 2 is implanted in the alveolar bone, a head part 3 coupled to an upper end portion of the main body 2, a first screw hole 4 that is hexagonal and in an upper surface of the head part 3, and a second screw hole 5 on a bottom surface of the first screw hole 4, to which the abutment for an implant may be screw-coupled.

In order to implant the dental implant fixture 1, as illustrated in FIG. 1, a treatment of forming an implant hole H in an alveolar bone B using a dental drill D is needed. Fenestration is performed as illustrated in FIG. 2 so as not to damage a dental nerve N inside the alveolar bone B or a cortical bone S that is an envelope of the alveolar bone B. Since a cancellous bone C inside the alveolar bone B characteristically has a relatively large supply of blood and is soft, the cancellous bone C, when damaged, has been known to have a restoration speed that is about 10 times faster than that of the cortical bone S that is characteristically relatively hard.

However, when the amount of the alveolar bone B is not sufficient at a buccal surface or a lingual surface or fenestration is performed close to the buccal surface or the lingual surface due to an error of an operator, the cortical bone S may be dehiscenced or fenestrated at one side surface or both side surfaces of the alveolar bone B as illustrated in FIGS. 3, 4, and 6.

In a case in which the implant hole H is ruptured (dehiscence) or formed (fenestration) in a side surface, when the dental implant fixture 1 is implanted as illustrated in FIG. 5, as a diameter of the dental implant fixture 1 is larger than a diameter of the implant hole H, the dental implant fixture 1 applies excessive pressure to the cortical bone S around the implant hole H. Accordingly, for a firm and stable implantation of the dental implant fixture 1, an alveolar bone ridge augmentation treatment needs to be further performed using a bone graft material 2 or a shield film 2.

To address the above problem, there is a demand for a fixture that does not apply excessive pressure to the cortical bone S of the alveolar bone B.

SUMMARY OF THE INVENTION

The present invention provides a dental implant fixture having an improved structure, which does not apply excessive pressure to a cortical bone of an alveolar bone when being inserted into an implantation hole, and is capable of rapidly regenerating the alveolar bone by accommodating a large amount of blood inside the implantation hole.

According to an aspect of the present invention, there is provided a dental implant fixture as a fixture implanted in an alveolar bone to be an artificial tooth root includes a main body vertically extending long along a center axis, at least part of the main body being implanted in the alveolar bone, and a cutting face formed on an outer circumferential surface of the main body to secure a space for accommodating blood when the main body is implanted in the alveolar bone.

The cutting face may be indented to be inwardly concave with respect to a virtual plane formed by cutting off an arc having a preset angle with respect to the center axis.

The cutting face may be a plane formed by cutting off an arc having a preset angle with respect to the center axis.

The cutting face may be vertically formed long along the center axis.

The cutting face may be formed in an area of about 80% to about 100% of a total length of the main body.

The cutting face may be formed in an area having an angle of about 60° to about 150° with respect to the center axis.

The cutting face may include a pair of concave surfaces arranged left and right with respect to a boundary line that is parallel to the center axis, and the boundary line may be vertically formed long along the center axis, protruding from the concave surfaces.

The cutting face may be provided in a pair to be arranged at opposite sides with respect to the center axis.

A bone graft material may be coupled to a surface of the cutting face with a preset thickness.

According to the present inventive concept, a dental implant fixture as a fixture implanted in an alveolar bone to be an artificial tooth root includes a main body vertically extending long along a center axis, at least part of the main body being implanted in the alveolar bone, and a cutting face formed on an outer circumferential surface of the main body to secure a space for accommodating blood when the main body is implanted in the alveolar bone.

The dental implant fixture does not apply excessive pressure to a cortical bone of an alveolar bone when being inserted into an implantation hole, and is capable of rapidly regenerating the alveolar bone by accommodating a large amount of blood inside the implantation hole.

DETAILED DESCRIPTION OF THE INVENTION

Hereinafter, embodiments of the present inventive concept are described in detail with reference to the accompanying drawings.

Figure 1:
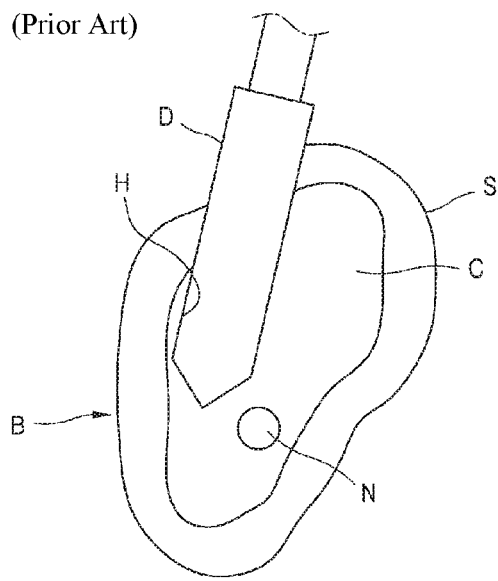
FIG. 1 is a vertical cross-sectional view illustrating a state in which an implant hole is formed in an alveolar bone by using a dental drill.
Figure 2:
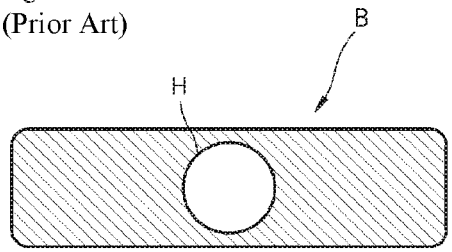
FIG. 2 is a horizontal cross-sectional view of the alveolar bone of FIG. 1 where the implant hole is formed.
Figure 3:
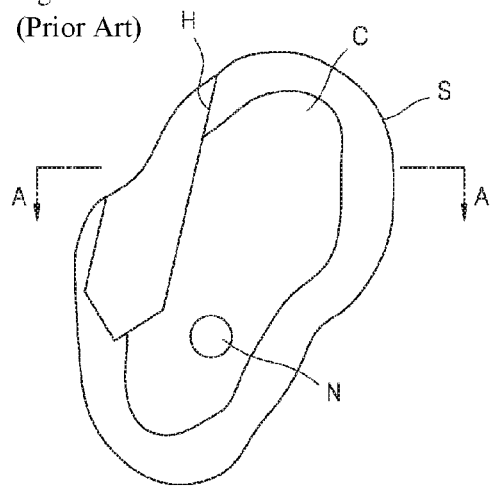
FIG. 3 is a vertical cross-sectional view illustrating a state in which an implant hole is formed by using a dental drill, rupturing a cortical bone at one side surface of an alveolar bone.
Figure 4:
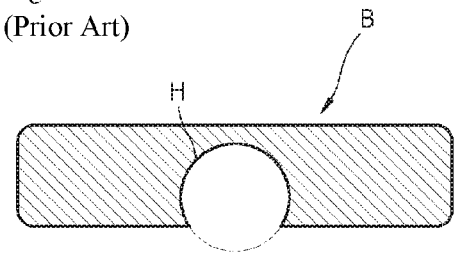
FIG. 4 is a cross-sectional view taken along a line A-A of FIG. 3 in the alveolar bone where the implant hole is formed.
Figure 5:
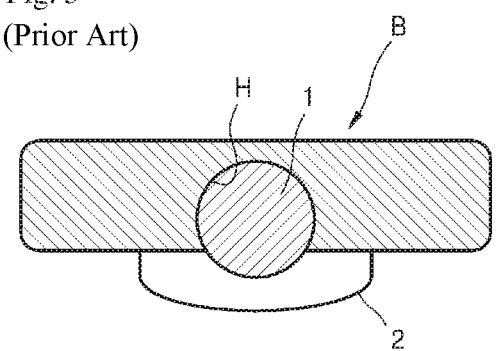
FIG. 5 illustrates a state in which a fixture according to a related art is inserted into the implant hole illustrated in FIG. 3 and an alveolar bone ridge augmentation treatment is performed using a bone graft material or a shield film.
Figure 6:
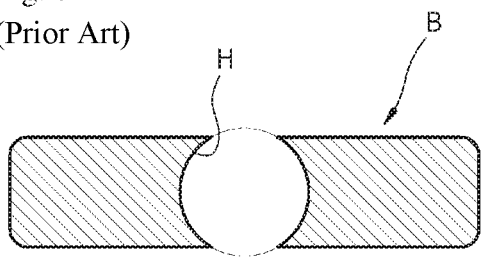
FIG. 6 illustrates a state in which a cortical bone at opposite side surfaces of an alveolar bone is ruptured by a dental drill.
Figure 7:
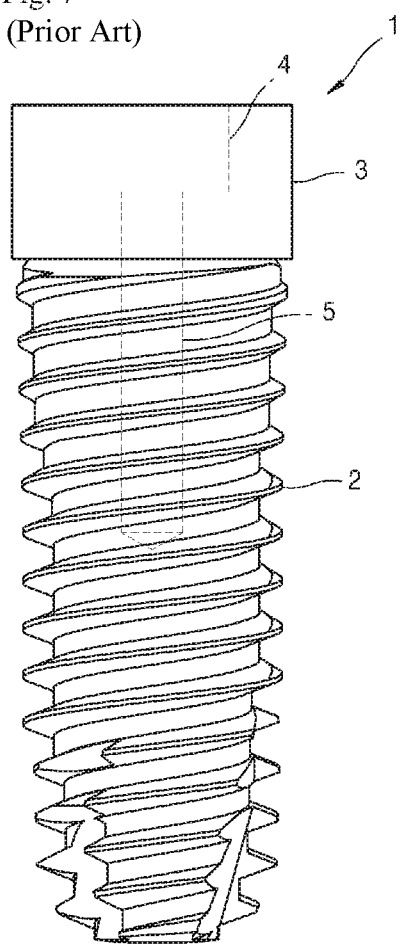
FIG. 7 illustrates an example of a dental implant fixture according to a related art.
Figure 8:
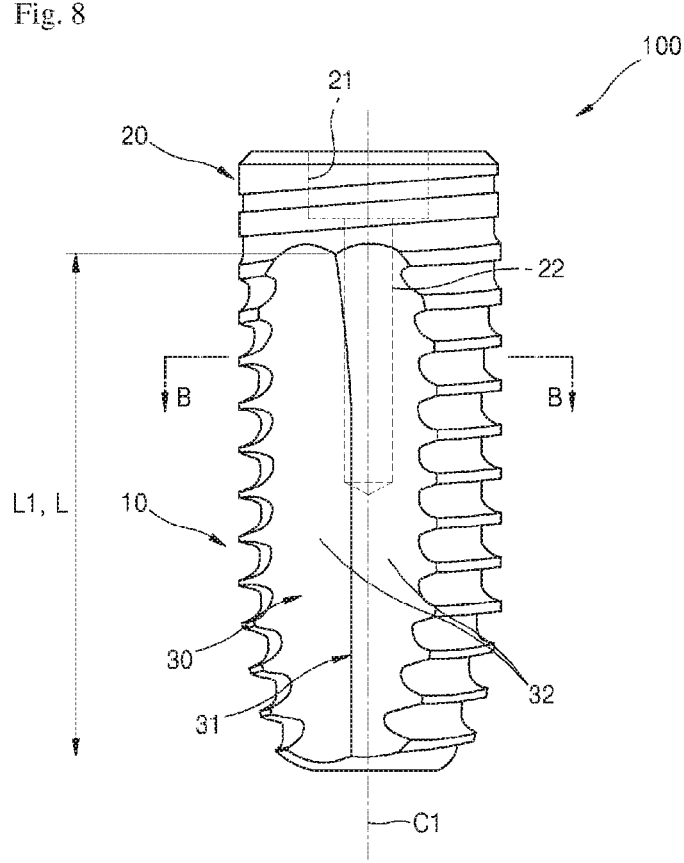
FIG. 8 illustrates a dental implant fixture according to an embodiment.
Figure 9:
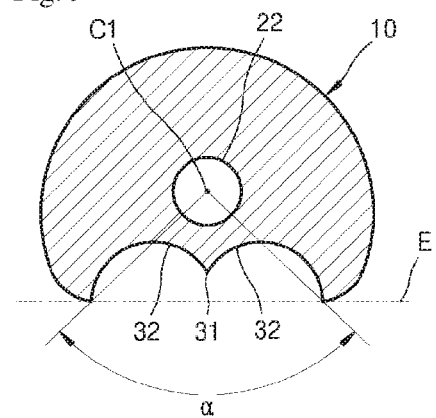
FIG. 9 is a cross-sectional view taken along a line B-B of FIG. 8 in the dental implant fixture.
Figure 10:
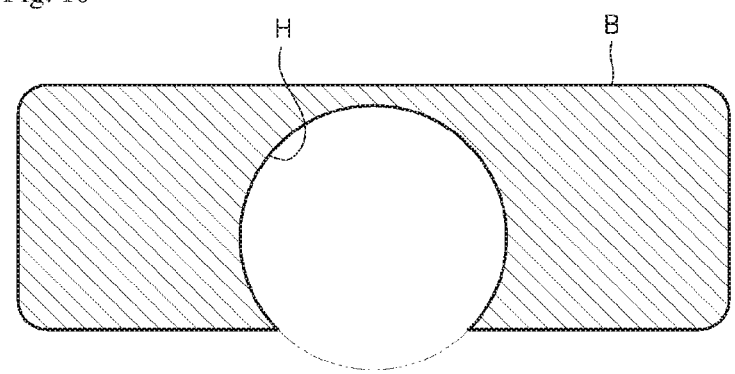
FIG. 10 is a horizontal cross-sectional view illustrating a state in which an implant hole is formed at one side surface of an alveolar bone, rupturing a cortical bone.

FIG. 8 illustrates a dental implant fixture according to an embodiment. FIG. 9 is a cross-sectional view taken along a line B-B of FIG. 8 in the dental implant fixture. FIG. 10 is a horizontal cross-sectional view illustrating a state in which an implant hole is formed at one side surface of an alveolar bone, rupturing a cortical bone.

Referring to FIGS. 8 to 10, a dental implant fixture 100 according to an embodiment is a fixture that is implanted in an alveolar bone B and becomes an artificial tooth root, and may include a main body 10, a head part 20, and a cutting face 30.

The main body 10, which is a cylindrical part vertically extending long along a center axis C1, has a male screw formed on at least a part of an outer circumferential surface thereof.

Figure 13:
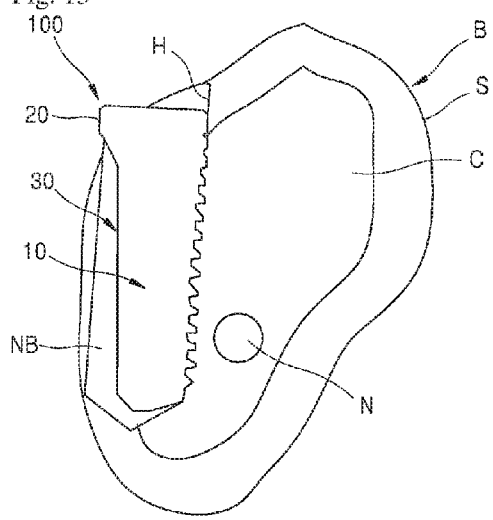
FIG. 13 is a vertical cross-sectional view of the dental implant fixture of FIG. 12.

The at least a part of the main body 10 is implanted in an implant hole H of the alveolar bone B and fixed thereto, as illustrated in FIGS. 10 and 13.

The head part 20, which is a cylindrical part having the center axis C1 as a center of a circle, is coupled to an upper end portion of the main body 10.

A first screw hole 21 is formed in an upper surface of the head part 20. The first screw hole 21 is a hexagonal screw hole into which a screw driver (not shown) for allowing the main body 10 to be rotatably inserted into the implant hole H of the alveolar bone B is mounted.

A second screw hole 22 is formed in a bottom surface of the first screw hole 21. An abutment for an implant that is an abutment post may be screw-coupled to the second screw hole 22.

The cutting face 30 is formed in the outer circumferential surface of the main body 10. The cutting face 30 is a portion to secure a space for accommodating blood P when the main body 10 is implanted in the implant hole H of the alveolar bone B.

The cutting face 30 includes a pair of concave surfaces 32 vertically formed long along the center axis C1. The concave surfaces 32 are arranged left and right with respect to a boundary line 31 parallel to the center axis C1.

The concave surfaces 32 are indented to be inwardly concave toward the center axis C1, based on a virtual plane E formed by cutting off an arc having a preset angle $\alpha$ with respect to the center axis C1.

The boundary line 31 is vertically formed long protruding from the concave surfaces 32 and is sharp as the concave surfaces 32 are discontinuously coupled to each other.

The angle $\alpha$ has a value of about 60° to about 150° with respect to the center axis C1, for example, about 100° in the present embodiment.

When the angle $\alpha$ is less than about 60°, a space for accommodating blood P secured by the cutting face 30 is insufficient. When the angle $\alpha$ exceeds about 150°, the main body 10 is not stably screw-coupled to the implant hole H.

It is appropriate that the cutting face 30 is formed in an area of about 80% to about 100% of a total length L1 of the main body 10. In the present embodiment, the cutting face 30 is formed in an area of about 100% of the total length L1 of the main body 10. In other words, the total length L1 of the main body 10 is the same as a length L of the cutting face 30.

When the length L of the cutting face 30 is less than about 80% of the total length L1 of the main body 10, the space for accommodating blood P secured by the cutting face 30 is insufficient. When the length L of the cutting face 30 exceeds about 100% of the total length L1 of the main body 10, which means that part of the cutting face 30 is formed in the head part 20, such a structure is not appropriate considering that the head part 20 is not generally inserted into the implant hole H.

Although the cutting face 30 is completely inserted into the implant hole H of the alveolar bone B, part of an upper end portion of the cutting face 30 may be exposed to the outside of the implant hole H.

In the following description, an example of a method of using the dental implant fixture 100 configured as above is described.

Figure 11:
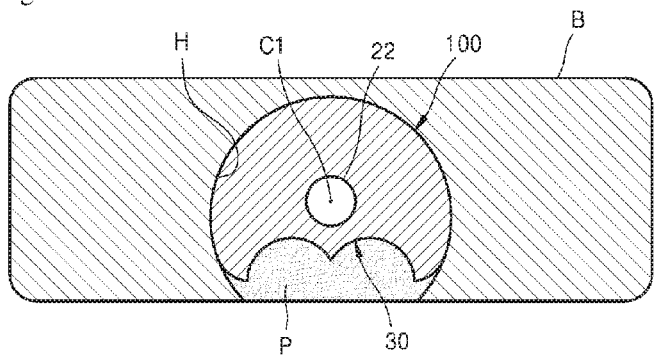
FIG. 11 illustrates a state in which the dental implant fixture of FIG. 8 is inserted into the implant hole of FIG. 10.

First, when the main body 10 is screw-coupled, by using a screw driver, to the implant hole H having a cortical bone S ruptured at one side surface of the alveolar bone B as illustrated in FIG. 10, the main body 10 is screw-coupled to the implant hole H as illustrated in FIG. 11. In this state, a rotation position of the main body 10 is adjusted so that the cutting face 30 faces a ruptured portion of the cortical bone S.

Figure 12:
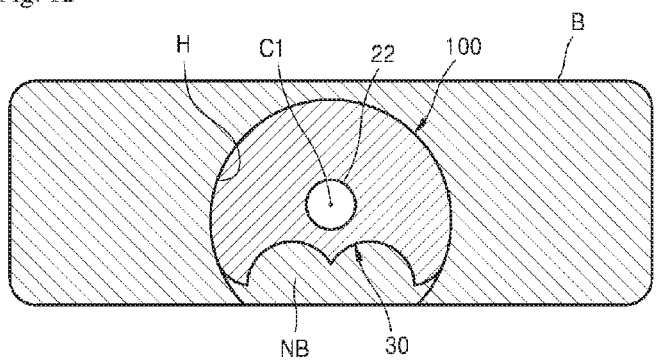
FIG. 12 illustrates a state in which the dental implant fixture of FIG. 11 is completely stably settled.

When a certain time period passes after the dental implant fixture 100 is implanted, the blood P of a human body is gathered and accommodated in the space formed by the cutting face 30 and an inner circumferential surface of the implant hole H, as illustrated in FIG. 11. When a long time period passes, new alveolar bone NB is formed in the space where the blood P is gathered, as illustrated in FIGS. 12 and 13, thereby completing the settlement of the dental implant fixture 100.

The dental implant fixture 100 configured as above vertically extends long along the center axis C1 and may include the main body 10, at least part thereof being implanted in the alveolar bone B, and the cutting face 30 formed in the outer circumferential surface of the main body 10 to secure the space for accommodating the blood P when the main body 10 is implanted in the alveolar bone B. Accordingly, when the main body 10 is inserted into the implant hole H, no excessive pressure is applied to the cortical bone S of the alveolar bone B, and a large amount of the blood P is accommodated in the implant hole H so that the alveolar bone B may be rapidly regenerated.

Since the cutting face 30 includes the concave surfaces 32 that are indented to be inwardly concave based on the virtual plane E formed by cutting off an arc having a preset angle α with respect to the center axis C1, the dental implant fixture 100 may accommodate a large amount of the blood P, compared to a case in which the cutting face 30 is plane.

Furthermore, since the cutting face 30 is formed vertically long along the center axis C1, the dental implant fixture 100 may accommodate a relatively large amount of the blood P. When being manufactured using a cutter, a cutting process may be easily performed.

Since the cutting face 30 is formed in an area of about 80% to about 100% of the total length L1 of the main body 10, the dental implant fixture 100 may easily secure the space for accommodating the blood P secured by the cutting face 30, necessarily for an implant treatment.

Furthermore, since the cutting face 30 is formed in an area of about 60° to about 150° with respect to the center axis C1, the dental implant fixture 100 may sufficiently have the space for accommodating the blood P secured by the cutting face 30 and simultaneously the main body 10 may be stably screw-coupled to the implant hole H by a sufficient screw-coupling force.

Since the cutting face 30 includes a pair of the concave surfaces 32 arranged left and right with respect to the boundary line 31 parallel to the center axis C1, and the boundary line 31 is vertically formed long along the center axis C1, protruding from the concave surfaces 32, compared to a case in which only one cutting face 30 is provided, the dental implant fixture 100 may have the space for accommodating the blood P having a relatively uniform thickness, and a resistance force to a rotation force around the center axis C1 increases when the dental implant fixture 100 is completely settled.

Figure 14:
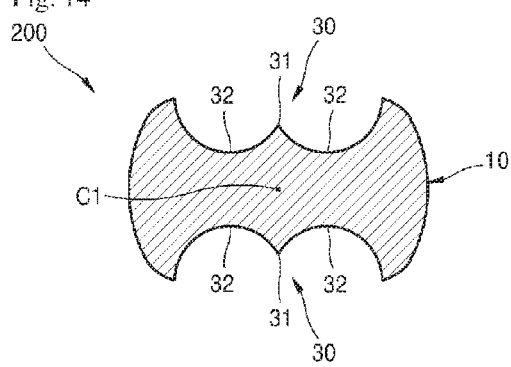
FIG. 14 is a horizontal cross-sectional view of a dental implant fixture according to another embodiment.

FIG. 14 is a horizontal cross-sectional view of a dental implant fixture 200 according to another embodiment. Since the structure and effect of the dental implant fixture 200 are almost the same as those of the dental implant fixture 100, in the following description, only differences therebetween are discussed.

The dental implant fixture 200 includes a pair of cutting faces 30 that are arranged at opposite sides with respect to the center axis C1.

Figure 15:
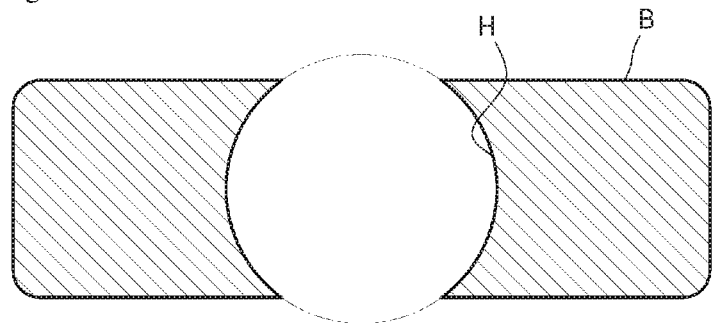
FIG. 15 is a horizontal cross-sectional view illustrating a state in which an implant hole is formed at opposite side surfaces of an alveolar bone, rupturing a cortical bone.

Accordingly, the dental implant fixture 200, as illustrated in FIG. 15, has a structure suitable for the implant hole H where the cortical bone S is ruptured at the opposite side surfaces of the alveolar bone B.

Figure 16:
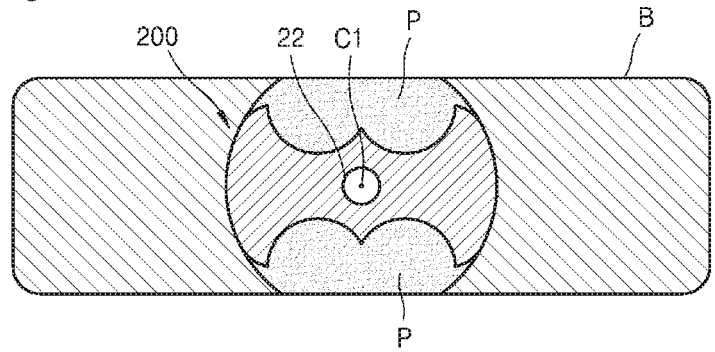
FIG. 16 illustrates a state in which the dental implant fixture of FIG. 14 is inserted into the implant hole of FIG. 15.
Figure 17:
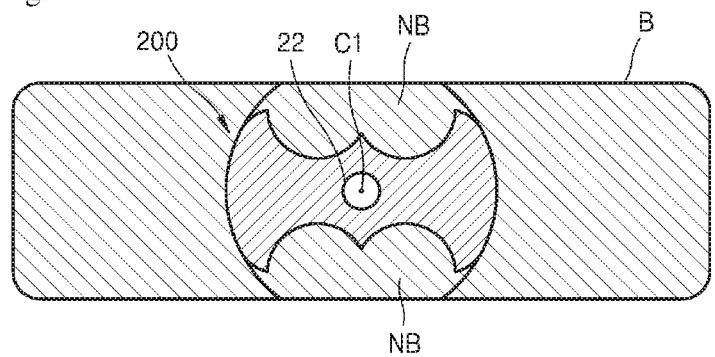
FIG. 17 illustrates a state in which the dental implant fixture of FIG. 16 is completely stably settled.

A treatment method of the dental implant fixture 200 is illustrated in FIGS. 15 to 17 and is almost the same as the treatment method of the dental implant fixture 100, and thus, a detailed description thereof is omitted.

Figure 18:
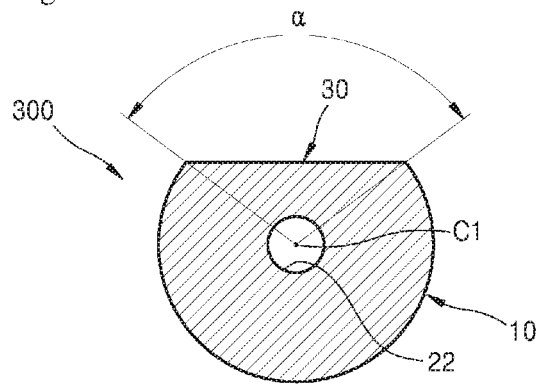
FIG. 18 is a horizontal cross-sectional view of a dental implant fixture according to another embodiment.

FIG. 18 is a horizontal cross-sectional view of a dental implant fixture 300 according to another embodiment. Since the structure and effect of the dental implant fixture 300 are almost the same as those of the dental implant fixture 100, in the following description, only differences therebetween are discussed.

Unlike the dental implant fixture 100 having the concave surfaces 32 indented to be inwardly concave, the dental implant fixture 300 includes the cutting face 30 having a plane shape obtained by cutting an arc having a preset angle α with respect to the center axis C1.

Accordingly, the dental implant fixture 300, compared to the dental implant fixture 100, may be easily cut-processed by a cutter, may be easily mass-produced, and may be easily recycled by processing the dental implant fixture 1 according to the related art.

Figure 19:
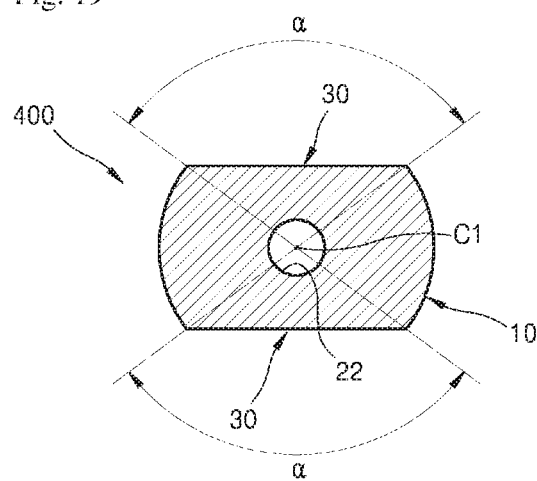
FIG. 19 is a horizontal cross-sectional view of a dental implant fixture according to another embodiment.

FIG. 19 is a horizontal cross-sectional view of a dental implant fixture 400 according to another embodiment. Since the structure and effect of the dental implant fixture 400 are almost the same as those of the dental implant fixture 100, in the following description, only differences therebetween are discussed.

The dental implant fixture 400 includes a pair of the cutting faces 30, each having a plane shape, which are arranged at opposite sides with respect to the center axis C1.

A treatment method of the dental implant fixture 400 is almost the same as the treatment method of the dental implant fixture 200, and thus, a detailed description thereof is omitted.

In the above-described embodiments, although the surface of the cutting face 30 is not coated with other materials, a graft material (not shown) may be coated on the surface of the cut-off pat 30 with a preset thickness.

The graft material may be formed by mixing powder formed of synthetic resin, animal bone, or human bone with an adhesive material exhibiting superior bio-adaptability, coating the mixed powder on the surface of the cutting face 30, and drying the powder.

For example, the graft material may be formed by using collagen in a slurry form generated by pulverizing collagen that is scleroprotein forming animal bone, cartilage, tooth, skin as well as scales of fish kneading, into a form of powder, and kneading the collagen powder thick by mixing the collagen powder with a certain amount of water.

The one or more embodiments described above are intended to exemplify the main concepts of the present inventive concept, and not limit the present inventive concept. It will be understood by one of ordinary skill in the art that various substitutions, amendments, or modifications may be made to the one or more embodiments of the present inventive concept without is departing from the spirit and scope of the present inventive concept.

The invention claimed is:

1. A dental implant fixture for use as a fixture implanted in an alveolar bone to be an artificial tooth root, the dental implant fixture comprising:
   a main body vertically extending long along a center axis and having a total length, at least part of the main body being intended to be implanted in the alveolar bone; and
   a cutting face formed on an outer circumferential surface of the main body, which is intended to provide a space for blood when the main body is implanted in the alveolar bone, the cutting face extending vertically along the main body and having a pair of vertically-extending concave surfaces which are inwardly concave and are separated by a protruding, vertically-extending boundary line that is parallel to the center axis, with the pair of concave surfaces located to the left and right of the boundary line, the concave surfaces and the boundary line having a length which is about 80% to about 100% of the total length of the main body and a width which is an arc of about 60° to about 150° of the main body.

2. The dental implant fixture of claim 1, having a pair of cutting faces arranged at opposite sides with respect to the center axis.

3. The dental implant fixture of claim 1, wherein a bone graft material is coupled to a surface of the cutting face with a preset thickness.

4. The dental implant fixture of claim 1, wherein the boundary line is sharp.

5. The dental implant fixture of claim 1, wherein the concave surfaces of the pair of vertically-extending concave surfaces have the same shape and size.

* * * * *